United States Patent [19]

Smith

[11] 4,091,041

[45] May 23, 1978

[54] PREPARATION OF 1,4-DIOLS BY HYDROLYSIS-HYDROGENATION OF 2-ALKOXYTETRAHYDROFURANS

[75] Inventor: William Edward Smith, Schenectady, N.Y.

[73] Assignee: General Electric Company, Pittsfield, Mass.

[21] Appl. No.: 806,074

[22] Filed: Jun. 13, 1977

[51] Int. Cl.$^2$ .............................................. C07C 29/00
[52] U.S. Cl. ................................ 568/865; 260/343.6; 260/347.8; 568/903; 568/904
[58] Field of Search .......................... 260/635 E, 343.6

[56] References Cited

U.S. PATENT DOCUMENTS

| | | | |
|---|---|---|---|
| 2,546,019 | 3/1951 | Smith | 260/635 E |
| 2,888,492 | 5/1959 | Fischer et al. | 260/635 E |
| 3,671,550 | 6/1972 | Hagemeyer et al. | 260/635 E |
| 3,773,842 | 11/1973 | Schirmann et al. | 260/635 E |
| 3,929,915 | 12/1975 | Cumbo et al. | 260/635 E |
| 3,966,827 | 6/1976 | Aquila et al. | 260/635 E |

OTHER PUBLICATIONS

Schniepp et al., "J. Am. Chem. Soc.," vol. 68, (1946), pp. 1646–1648.

*Primary Examiner*—Joseph E. Evans
*Attorney, Agent, or Firm*—Morgan, Finnegan, Pine, Foley & Lee

[57] ABSTRACT

2-alkoxytetrahydrofurans are converted to 1,4-diols under hydrolysis-hydrogenation conditions. The method may be coupled with the synthesis of 2-alkoxytetrahydrofurans to provide a highly efficient, two-step conversion of allylic alcohols to butanediols.

20 Claims, No Drawings

PREPARATION OF 1,4-DIOLS BY HYDROLYSIS-HYDROGENATION OF 2-ALKOXYTETRAHYDROFURANS

The present invention relates to a process for preparing 1,4-diols. More particularly, it is concerned with the conversion of 2-alkoxytetrahydrofurans to butanediols under hydrolysis-hydrogenation conditions.

BACKGROUND OF THE INVENTION

Although the hydrolysis-hydrogenation of aldehyde acetals derived from acrolein has been described in U.S. Pat. No. 3,929,915, incorporated herein by reference, there are no reports on the conversion of 2-alkoxytetrahydrofuran or its derivatives to 1,4-butanediols or the corresponding 1,4-substituted-butanediols under such conditions.

It has now been discovered that 2-alkoxytetrahydrofurans can be readily converted to the corresponding 1,4-butanediol and derivatives in high yield. The starting materials are obtained by a method described in concurrently filed U.S. application Ser. No. 806,073 by William Edward Smith entitled "2-Alkoxytetrahydrofurans Via Hydroformylation of Allylic Alcohol", and assigned to the same assignee as the instant application.

Typical reactions are outlined as follows:

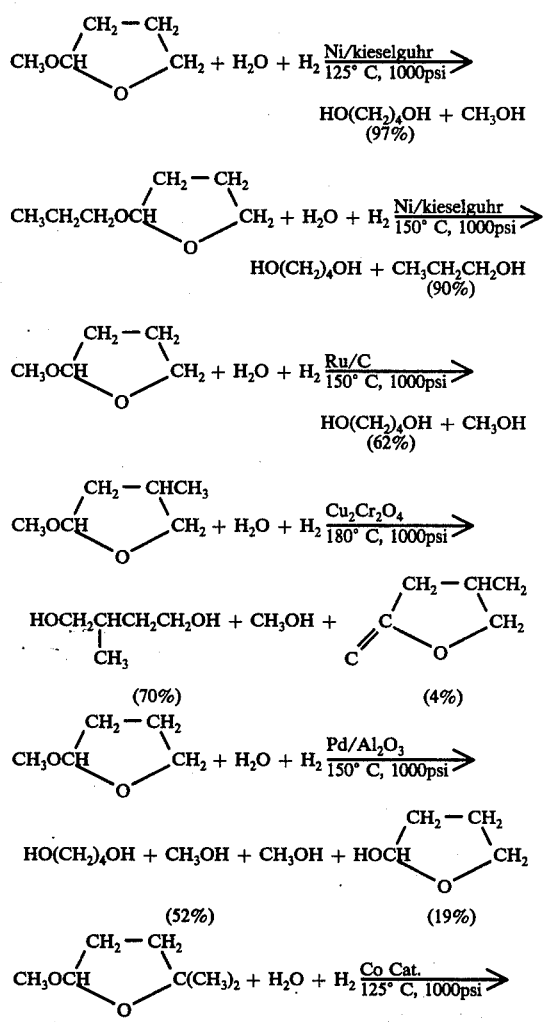

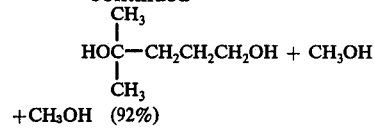

As indicated from the yield data (%), the process is particularly effective in providing high yields of valuable, polyester-forming butanediols. Furthermore, certain catalysts (pathways (4) and (5)) are also useful to co-produce corresponding lactones, which are valuable in their own right.

DESCRIPTION OF THE INVENTION

According to the present invention, there is provided a process for the production of a butanediol or a substituted butanediol which comprises contacting a 2-alkoxytetrahydrofuran or 2-alkoxy-substituted tetrahydrofuran with hydrogen in the presence of water and a hydrolysis-hydrogenation catalyst.

In preferred features the process will include the step of separating the product from the catalyst; carrying out the process in the liquid phase; carrying it out under super-atmospheric pressure, preferably in the range of 300 – 5000 psi and especially preferably in the range of 500 – 2000 psi.

In still another preferred feature the process will be carried out at an elevated temperature, preferably in the range of 100° – 200° C. The amount of water can vary broadly, but preferably will comprise from at least a trace to a substantial excess depending upon the amount of the alkoxy-tetrahydrofuran and especially preferred wherein the amount of water will comprise at least one equivalent per equivalent of the tetrahydrofuran.

Special mention is made of the process wherein the 2-alkoxytetrahydrofuran is selected from a compound of the general formula

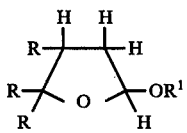

wherein R is, independently, hydrogen or alkyl of from 1 to 8 carbon atoms and $R^1$ is alkyl of from 1 to 8 carbon atoms. The carbon chains can be straight or branched, in any case.

Illustrative of such compounds are: 2-methoxytetrahydrofuran, 2-n-propoxytetrahydrofuran, 2-methoxy-4-methyltetrahydrofuran, 2-methoxy-5,5-dimethyltetrahydrofuran, and the like.

Among the catalysts which can be used in preferred embodiments are: ruthenium on carbon, nickel on kieselguhr, palladium on alumina, copper chromite, cobalt, or a derivative of the foregoing. The ruthenium and the copper chromite catalysts are found to promote the co-production of valuable by-product lactones. The others are preferred if highest yields of butanediols are desired.

In preferred features the present invention also contemplates embodiments wherein the 2-alkoxytetrahydrofurans or 2-alkoxy-substituted-tetrahydrofurans are produced by contacting an allylic alcohol, carbon monoxide, hydrogen and a corresponding alkanol with a rhodium hydroformylation catalyst. Such a technique is a highly efficient two-step conversion of allylic alcohols to butanediols.

The allylic alcohols include compounds characterized by the basic allylic alcohol structural arrangement:

$$C=C-C-OH$$

Examples of suitable allylic alcohols include allyl alcohol, methallyl alcohol, crotyl alcohol, cinnamyl alcohol, 2-butene-1,-4-diol and 3-hydroxycyclohexene. For further details, see the said copending application, which is incorporated herein by reference.

The process may be carried out under a wide variety of conditions, which are conventional for hydrolysis-hydrogenation reactions. These conditions are well known to those of ordinary skill in this art. Detailed examples are appended.

Moreover, a solvent may be employed to advantage in the disclosed process, preferably one which is inert with respect to the starting materials and products.

The process may be carried out batchwise or on a continuous or semicontinuous basis. Typically in a continuous or semicontinuous process, a mixture of the 2-alkoxytetrahydrofuran and water is passed through a bed of catalyst under hydrogen. Alternatively the reactants and the catalyst can be stirred in a pressure reactor. The diol products can be isolated from the catalyst by usual procedures, such as filtration followed by distillation.

DESCRIPTION OF THE PREFERRED EMBODIMENTS

The following examples illustrate the process of the invention. They are not to be construed to limit the claims in any manner whatsoever.

EXAMPLE 1

(a) 2-Methoxy-5,5-dimethyltetrahydrofuran

A 300 cc Autoclave Engineers Magnedrive autoclave is charged with 74.1 grams of 2-methyl-3-buten-2-ol (861 mmol), 75.0 grams of methanol (2.34 mol), 9.6 grams of triphenylphospine (36.6 mmol), and 0.20 grams of hexarhodium hexadecacarbonyl (0.188 mmol, 1.13 meq Rh). The mixture is subjected to 1200 psi of 1:1 $H_2/CO$ and heated to 150° C. In one hour a total of 5300 psi of 1:1 gas is taken up and replenished at 800 – 1200 psi.

Analysis of the product mixture shows the presence of a very large proportion of a compound subsequently characterized and identified as 2-methoxy-5,5-dimethyltetrahydrofuran. According to quantitative glpc analysis (Apiezon column, vs. diphenylmethane internal standard) the yield of this product is 105.5 grams, 94% of the theoretical amount. The structure assignment is confirmed by IR, $^1$H nmr and mass spectra obtained on the isolated compound. A sample of greater than 99% purity is obtained by distillation (bp 126° C).

(b) 4-Methyl-1,4-pentanediol

A 300 cc Autoclave Engineers Magnedrive autoclave is charged with 34.8 grams of 2-methoxy-5,5-dimethyltetrahydrofuran derived from 2-methyl-3-buten-2-ol as described in step (a), 35 ml of water and 5.0 grams of powdered cobalt catalyst (Harshaw' Co-1606, 85% cobalt on an alkaline support). The mixture is subjected to 1000 psi of hydrogen and heated at 125° C for 1.5 hours. Analysis (glpc) of the product mixture shows that the starting material has been completely converted to the diol and methanol. The catalyst is filtered off, and the filtrate is concentrated by rotary vacuum evaporation, leaving 29.1 grams of 4-methyl-1,4-pentanediol (92% yield). The IR spectrum of the product thus isolated is identical with that of the fully characterized, glpc-purified compound.

EXAMPLE 2

(a) 2-Methoxytetrahydrofuran

The autoclave is charged with 50.0 grams of allyl alcohol (861 mmol), 75.0 grams of methanol (2.34 mol), 0.20 grams of hexarhodium hexadecacarbonyl (0.188 mmol, 1.13 meq Rh), and 11.2 grams of triphenylarsine (36.6 mmol). The mixture is heated at 130° – 135° C. under replenished 900 – 1200 psi 1:1 $H_2/CO$ for 45 minutes (3700 psi total uptake), then cooled and analyzed. The presence of 46.6 grams of 2-methoxytetrahydrofuran (53% yield) is indicated.

(b) 1,4-Butanediol

A methanolic hydroformylation product mixture obtained as described in step (a) is distilled through a short path head to provide a co-distillate (boiling range 65° – 78° C) of which methanol and 2-methoxytetrahydrofuran (25% by weight according to quantitative glpc analysis) were the major components. The autoclave is charged with 50.0 grams of the co-distillate containing 12.3 grams of 2-methoxytetrahydrofuran, 50 ml of water and 5.0 grams of powdered Girdler G-69 nickel catalyst (50% Ni on kieselguhr support, reduced and stabilized). The mixture is subjected to 1000 psi of hydrogen and heated at 125° C for 30 minutes. The gas uptake corresponds to 350 psi.

The product mixture is filtered and subjected to quantitative glpc analysis, which shows the presence of 10.5 grams of 1,4-butanediol (97% yield) as well as traces of the 2-hydroxytetrahydrofuran intermediate and 2-methoxytetrahydrofuran starting material. Some propanol is also formed by hydrogenation of propionaldehyde present in the starting co-distillate.

EXAMPLE 3

1,4-Butanediol and 4-butyrolactone

The autoclave is charged with 60.0 grams of a methanolic co-distillate (boiling range 58° – 67° C) containing 14.6 grams of 2-methoxytetrahydrofuran, 30 ml of water and 3.0 grams of powdered 0.5% ruthenium on carbon (Engelhard). The mixture is heated under 1000 psi at 125° C for 30 minutes and at 150° C for 2 hours. In the latter period gas corresponding to 620 psi is taken up.

Analysis of the products shows the presence of 8.0 grams of 1,4-butanediol (62% yield) and 1.2 grams of 4-butyrolactone (10% yield). Also detected were n-propanol and isobutanol formed by hydrogenation of the corresponding aldehydes present in the starting co-distillate.

EXAMPLE 4

1,4-Butanediol

The process is carried out as in Examples 1 – 3 using 50.0 grams of a methanolic co-distillate (boiling range 65°–78° C) containing 12.3 grams of 2-methoxytetrahydrofuran, 50 ml of water and 5.0 grams of powdered 0.5% palladium on active alumina (Engelhard). The mixture is heated at 150° C under 1000 psi of hydrogen for 2 hours, then cooled and analyzed. The presence of 2.5 grams of 2-methoxytetrahydrofuran (20% unconverted), 4.5 grams of 1,4-butanediol (52% yield based on 80% conversion) and 1.6 grams of 2-hydroxytetrahydrofuran intermediate (19% yield based on 80% conversion of the starting material) is indicated.

EXAMPLE 5

1,4-Butanediol

The autoclave is charged with 11.5 grams of distillate (bp 145° C) containing 10.4 grams of 2-n-propoxytetrahydrofuran, 50 ml of water and 1.0 grams of the nickel catalyst described in Example 2. The mixture is heated under 1000 psi of hydrogen at 150° C for 30 minutes, then cooled and analyzed. The presence of 6.5 grams of 1,4-butanediol (90% yield) and an approximately corresponding amount of n-propanol is indicated. Also detected is 0.34 grams of 2-methyl-1,3-propanediol produced by hydrogenation of 3-hydroxy-2-methylpropionaldehyde present in the starting material.

EXAMPLE 6

(a) 2-Methoxy-4-methyltetrahydrofuran

The autoclave is charged with 62.2 grams of methallyl alcohol (861 mmol), 50.0 grams of methanol 1.56 mol), 0.20 grams of hexarhodium hexadecacarbonyl (0.188 mmol, 1.13 meq Rh), and 11.2 grams of triphenylarsine (36.6 mmol), then pressurized to 1200 psi with 1:1 $H_2$/CO and heated to 125° C. In about 1 hour from onset of reaction a total of 3300 psi of 1:1 gas is taken up and replenished at 900 – 1200 psi. The product mixture is cooled and subjected to quantitative glpc analysis (diphenylmethane internal standard, relative response factors determined using product isolated by glpc). The presence of 75.9 grams of 2-methoxy-4-methyltetrahydrofuran is indicated (76% yield). The structure assignment is in accord with the IR, $^1$H nmr and mass spectra of the isolated product.

(b) 2-Methyl-1,4-butanediol and 3-methyl-4-butyrolactone

The process is carried out as in Examples 1 – 5 using 50.0 grams of a methanolic co-distillate (boiling range 66° – 78° C) containing 14.8 grams of 2-methoxy-4-methyltetrahydrofuran derived from methallyl alcohol as described in step (a), 30 ml of water and 5.0 grams of powdered copper chromite (Catalysts and Chemicals Co.). The mixture is heated at 180° C under 1000 psi of hydrogen for one hour. Analysis of the product mixture shows the presence of 9.3 grams of 2-methyl-1,4-butanediol (70% yield) and about 0.5 grams of 3-methyl-4-butyrolactone (4% yield).

The identities of the diol, lactone and lactol products described above were verified by analysis of their infrared (IR) and mass spectra and comparison with those of the authentic materials.

It is seen that the method of this invention provides an efficient, integrated two-step conversion of allyl alcohol and congeners to 1,4-butanediol and its congeners. The steps are fundamentally integrated in that the alkanol component taken up in the first step is released in the second step for recycle (Equations 7 and 8).

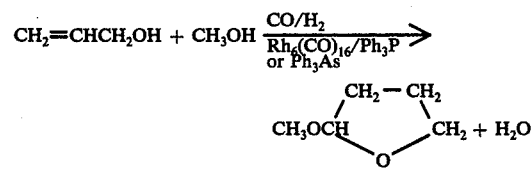

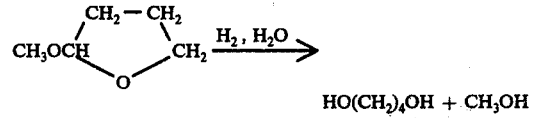

The process is further integrated with respect to separation of the 2-methoxytetrahydrofuran and congeners from the catalyst at modest temperatures as a co-distillate with methanol or other low boiling alcohols such as ethanol and isopropanol.

The formation of 4-butyrolactone (Equation 3) and 3-methyl-4-butyrolactone (Equation 4) under conditions of relatively high hydrogen pressure is strong evidence that the 2-alkoxytetrahydrofurans may be readily converted to the corresponding lactones under hydrolysis-dehydrogenation conditions (Equation 9).

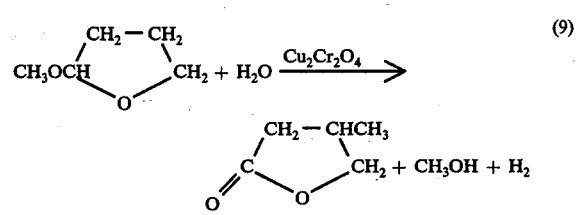

The apparent propensity of the intermediate lactol to undergo dehydrogenation makes it further possible that such a process is easily carried out without the occurrence of simultaneous dehydrogenation of the alkanol product.

Obviously, minor variations will suggest themselves to those skilled in the art in view of the above-detailed description. All such obvious modifications are within the full intended scope of the appended claims.

I claim:

1. A process for the production of butanediol or substituted-butanediols which comprises contacting a 2-alkoxy-tetrahydrofuran or 2-alkoxy-substituted tetrahydrofuran with hydrogen in the presence of water and a hydrolysis-hydrogenation catalyst.

2. A process as defined in claim 1 including the step of separating the product from the catalyst.

3. A process as defined in claim 1 carried out in the liquid phase.

4. A process as defined in claim 1 carried out under super-atmospheric pressure.

5. A process as defined in claim 4 wherein said pressure is in the range of 300 – 5000 psi.

6. A process as defined in claim 5 wherein said pressure is in the range of 500 – 2000 psi.

7. A process as defined in claim 1 carried out at an elevated temperature.

8. A process as defined in claim 7 wherein said temperature is in the range of 100° – 200° C.

9. A process as defined in claim 1 wherein the amount of water comprises from at least a trace to a substantial excess based on the amount of said tetrahydrofuran.

10. A process as defined in claim 9 wherein the amount of water comprises at least one equivalent per equivalent of said tetrahydrofuran.

11. A process as defined in claim 1 wherein said 2-alkoxytetrahydrofuran or 2-alkoxy-substituted-tetrahydrofuran is selected from a compound of the general formula:

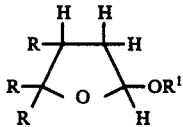

wherein R is hydrogen or alkyl of from 1 to 8 carbon atoms and $R^1$ is alkyl of from 1 to 8 carbon atoms.

12. A process as defined in claim 11 wherein said compound is 2-methoxytetrahydrofuran, 2-n-propoxytetrahydrofuran, 2-methoxy-4-methyltetrahydrofuran or 2-methoxy-5,5-dimethyltetrahydrofuran.

13. A process as defined in claim 12 wherein said compound is 2-methoxytetrahydrofuran, and said catalyst comprises ruthenium on carbon and minor amounts of the corresponding lactone are co-produced with said 1,4-diol.

14. A process as defined in claim 12 wherein said compound is 2-methoxytetrahydrofuran and said catalyst comprises nickel on kieselguhr.

15. A process as defined in claim 12 wherein said compound is 2-n-propoxytetrahydrofuran and said catalyst comprises nickel on kieselguhr.

16. A process as defined in claim 12 wherein said compound comprises 2-methoxytetrahydrofuran and said catalyst comprises palladium on alumina.

17. A process as defined in claim 12 wherein said compound comprises 2-methoxy-4-methyltetrahydrofuran, said catalyst comprises copper chromite and minor amounts of the corresponding lactone are co-produced with said diol.

18. A process as defined in claim 12 wherein said compound comprises 2-methoxy-5,5-dimethyltetrahydrofuran and said catalyst comprises cobalt.

19. A process as defined in claim 1 which also includes the step of preparing said 2-alkoxytetrahydrofuran or 2-alkoxy-substituted-tetrahydrofuran by contacting an allylic alcohol, carbon monoxide, hydrogen and a corresponding alkanol with a rhodium hydroformylation catalyst.

20. A process as defined in claim 19 wherein said allylic alcohol comprises allyl alcohol, methallyl alcohol or 2-methyl-3-buten-2-ol and said alkalol comprises methanol or n-propanol.

* * * * *

UNITED STATES PATENT AND TRADEMARK OFFICE
CERTIFICATE OF CORRECTION

PATENT NO. : 4,091,041
DATED : May 23, 1978
INVENTOR(S) : William Edward Smith

It is certified that error appears in the above-identified patent and that said Letters Patent are hereby corrected as shown below:

Column 1, Line 40, in the formula, "(90%)" should be below the portion that reads "HO(CH$_2$)$_4$OH" and not under the other portion.

, Lines 52-53, after the second "+", the formula should read as follows:

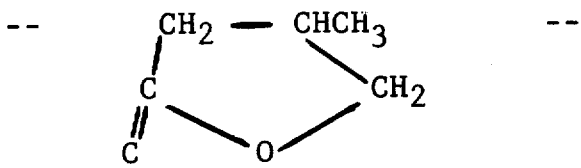

Column 2, Lines 5-6, delete the "+CH$_3$OH" that stands beside "(92%)"

UNITED STATES PATENT AND TRADEMARK OFFICE
CERTIFICATE OF CORRECTION

PATENT NO. : 4,091,041  
DATED : May 23, 1978  
INVENTOR(S) : William Edward Smith Page 2 of 2

It is certified that error appears in the above-identified patent and that said Letters Patent are hereby corrected as shown below:

Column 6, Lines 20-23, the beginning portion of the formula should read as follows:

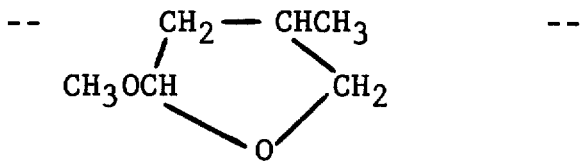

Column 8, Line 23, "alkalol" should read -- alkanol --.

Signed and Sealed this

*Twenty-third* Day of *January 1979*

[SEAL]

Attest:

RUTH C. MASON  
*Attesting Officer*

DONALD W. BANNER  
*Commissioner of Patents and Trademarks*